United States Patent
Mak

(10) Patent No.: US 9,132,379 B2
(45) Date of Patent: Sep. 15, 2015

(54) CONFIGURATIONS AND METHODS FOR GAS CONDENSATE SEPARATION FROM HIGH-PRESSURE HYDROCARBON MIXTURES

(75) Inventor: John Mak, Santa Ana, CA (US)

(73) Assignee: FLUOR TECHNOLOGIES CORPORATION, Aliso Viejo, CA (US)

( * ) Notice: Subject to any disclaimer, the term of this patent is extended or adjusted under 35 U.S.C. 154(b) by 1323 days.

(21) Appl. No.: 12/446,672

(22) PCT Filed: Nov. 6, 2007

(86) PCT No.: PCT/US2007/023449
§ 371 (c)(1),
(2), (4) Date: Apr. 27, 2009

(87) PCT Pub. No.: WO2008/060417
PCT Pub. Date: May 22, 2008

(65) Prior Publication Data
US 2010/0000255 A1    Jan. 7, 2010

Related U.S. Application Data

(60) Provisional application No. 60/865,126, filed on Nov. 9, 2006.

(51) Int. Cl.
*C10G 5/00* (2006.01)
*C10G 5/04* (2006.01)
(Continued)

(52) U.S. Cl.
CPC ................ *B01D 53/14* (2013.01); *C10G 21/00* (2013.01); *C10L 3/10* (2013.01); *C10L 3/12* (2013.01);
(Continued)

(58) Field of Classification Search
CPC .. C10G 5/04; C10G 2300/1025; C10G 21/00; C07C 7/156; C07C 7/152; B01D 2258/0216; B01D 47/06; B01D 53/1418; B01D 53/1487; C10L 3/12; C10L 3/102–3/104
USPC ............. 62/617, 618, 620, 622, 98, 625, 630, 62/632, 635; 95/191, 206, 207, 92, 94; 585/800, 867; 208/341, 346, 92, 96, 208/100, 101, 208 R, 209, 337, 351, 368; 96/243; 202/158, 168; 203/87, 98
See application file for complete search history.

(56) References Cited

U.S. PATENT DOCUMENTS 2,782,141 A * 2/1957 King ............................ 208/342
2,849,371 A * 8/1958 Gilmore ........................ 95/180
(Continued)

FOREIGN PATENT DOCUMENTS

EP    0612968 A1    8/1994
EP    0612968 B1    8/1994
(Continued)

*Primary Examiner* — John F Pettitt
*Assistant Examiner* — Tareq Alosh
(74) *Attorney, Agent, or Firm* — Fish & Tsang, LLP

(57) ABSTRACT

Contemplated configurations and methods for gas processing use a refluxed absorber that receives a liquid and a vapor hydrocarbon feed. The absorber further receives a stripping medium that is at least in part formed from a vapor portion of a stabilizer overhead and also receives a scrubbing medium that is at least in part formed from a liquid portion of the stabilizer overhead. Most preferably, the absorber overhead is maintained at a temperature near or even below the hydrate point of the feed.

17 Claims, 3 Drawing Sheets

(51) Int. Cl.

| | | |
|---|---|---|
| *C07C 7/00* | (2006.01) | |
| *B01D 59/26* | (2006.01) | |
| *B01D 53/14* | (2006.01) | |
| *C10G 21/00* | (2006.01) | |
| *C10L 3/12* | (2006.01) | |
| *B01D 47/06* | (2006.01) | |
| *C07C 7/152* | (2006.01) | |
| *C07C 7/156* | (2006.01) | |
| *C10L 3/10* | (2006.01) | |

(52) U.S. Cl.
CPC ............. *B01D 47/06* (2013.01); *B01D 53/1418* (2013.01); *B01D 53/1487* (2013.01); *B01D 2256/24* (2013.01); *B01D 2258/0216* (2013.01); *C07C 7/152* (2013.01); *C07C 7/156* (2013.01); *C10G 5/04* (2013.01); *C10G 2300/1025* (2013.01); *C10L 3/102* (2013.01); *C10L 3/104* (2013.01)

(56) References Cited

U.S. PATENT DOCUMENTS

| | | | |
|---|---|---|---|
| 3,247,649 A * | 4/1966 | Miller | 95/186 |
| 3,555,837 A * | 1/1971 | McClintock | 62/625 |
| 3,574,089 A | 4/1971 | Forbes | |
| 3,926,742 A * | 12/1975 | Anderson | 203/3 |
| 4,462,813 A | 7/1984 | May | |
| 4,507,133 A | 3/1985 | Khan | |
| 4,587,373 A * | 5/1986 | Hsia | 585/639 |
| 4,657,571 A * | 4/1987 | Gazzi | 62/621 |
| 4,696,688 A * | 9/1987 | Mehra | 62/625 |
| 4,702,819 A | 10/1987 | Sharma | |
| 4,743,282 A | 5/1988 | Mehra | |
| 5,685,170 A * | 11/1997 | Sorensen | 62/625 |
| 6,553,784 B2 * | 4/2003 | Lu | 62/632 |
| 6,658,893 B1 | 12/2003 | Mealey | |
| 6,662,589 B1 * | 12/2003 | Roberts et al. | 62/425 |
| 2003/0221447 A1 | 12/2003 | Mealey | |
| 2004/0261452 A1 * | 12/2004 | Mak et al. | 62/620 |
| 2005/0066686 A1 | 3/2005 | Wilkinson | |
| 2005/0255012 A1 | 11/2005 | Mak | |
| 2006/0089519 A1 | 4/2006 | Stell et al. | |

FOREIGN PATENT DOCUMENTS

| | | |
|---|---|---|
| GB | 2398624 | 12/2005 |
| WO | 2006014242 | 2/2006 |

* cited by examiner

Prior Art Figure 1

CONFIGURATIONS AND METHODS FOR GAS CONDENSATE SEPARATION FROM HIGH-PRESSURE HYDROCARBON MIXTURES

This application claims priority to our U.S. provisional patent application with the Ser. No. 60/865,126, which was filed Nov. 9, 2006.

FIELD OF THE INVENTION

The field of the invention is gas processing, especially as it relates to separation of gas condensate from a high-pressure vapor liquid mixture.

BACKGROUND OF THE INVENTION

Processing of high-pressure hydrocarbon mixtures is often problematic, and especially where such mixtures contain relatively large quantities of C5 and heavier components, and particularly C6+ BTEX hydrocarbons (i.e., benzene, toluene, and xylenes) and organic sulfur contaminants (e.g., ethyl-, propyl- and butylmercaptans and heavy thiosulfides). For example, associated gas production often contains residual amount of the C6+ heavy hydrocarbons and sulfur contaminants which often create downstream operating problems, and especially foaming and corrosion. Still further, C6+ heavy hydrocarbons and sulfur contaminants also tend to cause off-specification products in the acid gas removal units.

Therefore, numerous processing configurations and methods have been developed to treat high-pressure hydrocarbon mixtures. However, all or almost all of them fail to produce a C6+ condensate and a product gas void of the C6+ and sulfur contaminants to meet current stringent sulfur specifications. For example, U.S. Pat. No. 4,702,819 to Sharma et al. teaches use of dual fractionation zones wherein the first fractionation zone employs a side reboiler and a vapor side-stream. Such configurations allow for at least somewhat desirable levels of gas/liquid separation, however, the separation of the C5 components from the C6+ and sulfur contaminants at high pressure is often very difficult if not impossible as the relative volatility between the C5 to C6 hydrocarbons dramatically decreases at high pressures.

In another known configuration, as exemplified in U.S. Pat. No. 4,462,813 to May et al., a multi-stage compressor is connected to a wellhead, refrigeration unit, and separators. Similar to Sharma's configuration, May's configuration is relatively inefficient and energy demanding, and not suitable for high recovery of the C6+ hydrocarbons from the feed gas, particularly when processing high-pressure hydrocarbon mixtures comprising significant quantities of C6+ and sulfur contaminants.

In still further known examples, as described in RE 33,408 or U.S. Pat. No. 4,507,133 to Khan et al., the vapor stream from a deethanizer is cooled to liquefaction and contacted with a vapor phase from the hydrocarbon feed stream to separate methane, ethane, and propane vapors from the feed. Similarly, as described in U.S. Pat. No. 6,658,893 to Mealey, the feed gas is cooled to liquefy the heavier components and at least some of the C2 and lighter components. Subsequent condensation and absorption steps then allow high recovery of LPG components (i.e., C3 and C4+). Such processes are often limited to high yields of C3 and C4+ components, and are not suitable for C6+ condensates recovery.

Thus, while numerous configurations and methods for gas condensate hydrocarbon separation are known in the art, all or almost all of them suffer from one or more disadvantages. Therefore, there is still a need for improved configurations and methods for gas condensate separation, and especially for gas condensate separation from high-pressure hydrocarbon mixtures comprising significant quantities of the C6+ and sulfur contaminants.

SUMMARY OF THE INVENTION

The present invention is directed to plant configurations and methods in which NGL are separated from high-pressure feed gases in a manner such that the feed gas is stripped in a refluxed absorber by hot and compressed stabilizer overhead vapor and scrubbed by a lean oil stabilizer liquid. Most preferably, the absorber is operated near or even below the hydrate point of the feed gas.

In one aspect of the inventive subject matter, a method of processing a hydrocarbon feed (typically comprising at least 0.5 mol % of C6+ hydrocarbons) will include a step of feeding a vapor portion and a liquid portion of a high pressure hydrocarbon feed to a refluxed absorber, and maintaining an overhead temperature of the absorber at about or below hydrate temperature of the feed. In such methods, a stripping medium is fed to the absorber, wherein the stripping medium is at least in part formed from a vapor portion of a stabilizer overhead, and a scrubbing medium is fed to the absorber, wherein the scrubbing medium is at least in part formed from a liquid portion of the stabilizer overhead.

Most typically, the stripping medium further comprises a vapor portion of a bottom product of the absorber, and is compressed by a compressor prior to entry into the absorber. The scrubbing medium preferably comprises a vapor portion of a bottom product of the absorber. As the absorber produces a C6+ enriched bottom product and a C6+ depleted overhead product, it is contemplated that the C6+ enriched bottom product is separated in a first separator into a liquid portion of the C6+ enriched bottom product and a vapor portion of the C6+ enriched bottom product, art that the liquid portion of the C6+ enriched bottom product is fed to the stabilizer. In such methods and configurations, it is generally preferred that the vapor portion of the C6+ enriched bottom product is fed to a second separator.

In additional aspects of the inventive subject matter, it is contemplated that the stabilizer overhead is fed to the second separator. Where desirable, it is also contemplated to add a dehydrating section to the absorber and to maintain the overhead temperature of the absorber below hydrate temperature of the feed. Most typically, the reflux is provided by condensation of the absorber overhead, and the high pressure hydrocarbon feed has a pressure of between 800 and 1200 psig. Thus, preferred absorber pressures will typically be at about or above 800 psig.

Consequently, in another aspect of the inventive subject matter, a gas treatment plant will include a refluxed absorber that receives a C6+ containing feed gas at a pressure of equal to or greater than 600 psig, and that further produces a C6+ enriched bottom product and a C6+ depleted overhead product. A first separator is fluidly coupled to the refluxed absorber to receive the C6+ enriched bottom product and produces a liquid portion of the C6+ enriched bottom product and a vapor portion of the C6+ enriched bottom product. Additionally, a stabilizer is fluidly coupled to the first separator and receives the liquid portion of the C6+ enriched bottom product and produces an overhead, and a second separator is fluidly coupled to the stabilizer and receives the overhead and produces a vapor portion of the overhead and a liquid portion of the overhead, wherein the absorber receives the vapor portion of the overhead as stripping medium and receives the liquid portion of the overhead as a scrubbing medium.

In especially preferred aspects, a first compressor is fluidly coupled to the second separator and compresses the vapor portion of the overhead prior to entry into the absorber, and/or a conduit is fluidly coupled to the first and second separators to feed the vapor portion of the C6+ enriched bottom product from the first separator to the second separator. Where desired, a pressure reduction device (e.g., JT-valve, expander, etc.) is fluidly coupled to the absorber and first separator and configured to provide a flashed C6+ enriched bottom product to the first separator, and a cooler and separator are fluidly coupled to the absorber to receive and cool the C6+ depleted overhead product to thereby form a reflux stream to the absorber.

It is further generally preferred that the cooler is configured to cool the C6+ depleted overhead product to about hydrate temperature, and that a second compressor fluidly coupled to the stabilizer compresses the vapor portion of the overhead prior to entry into the second separator. Where desired, a glycol dehydration unit may be provided to the absorber, which is preferably operated at a pressure of about 1000 psig to 1200 psig. Most typically, the refluxed absorber is configured to separately receive a vapor portion of a feed gas and a liquid portion of the feed gas at separate trays.

Various objects, features, aspects and advantages of the present invention will become more apparent from the following detailed description of preferred embodiments of the invention along with the accompanying drawing.

BRIEF DESCRIPTION OF THE DRAWING

Prior Art

DETAILED DESCRIPTION

Figure 1:
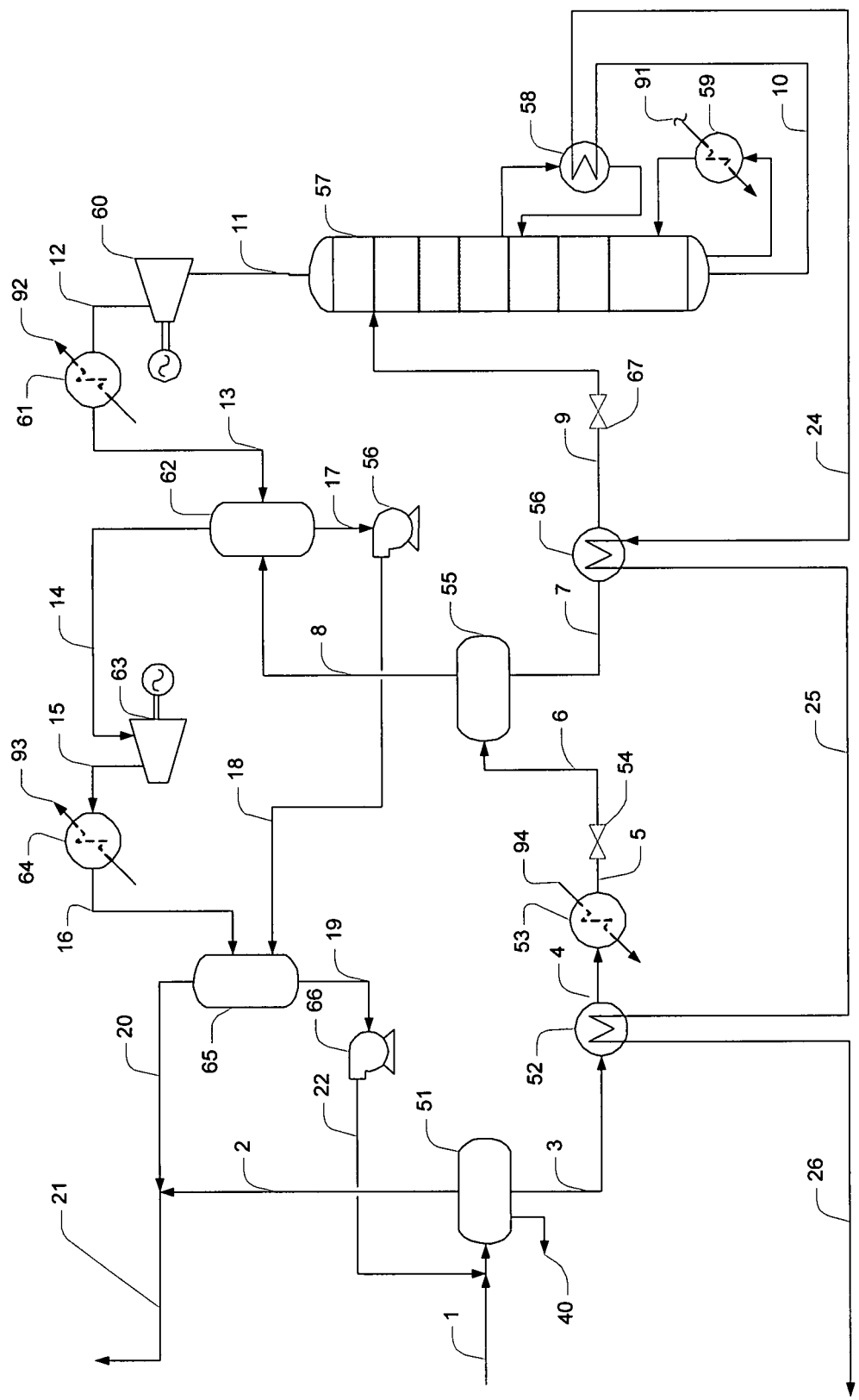
FIG. 1 is a schematic configuration of a known NGL plant.

The inventor has now discovered that configurations and methods for separation of gas condensates from high pressure (typically greater 600 psig, more typically greater than 800 psig) hydrocarbon feeds can be realized in a simple and effective manner, and that such configurations and methods are especially suitable where the hydrocarbon feed contains significant quantities of C6+ (typically greater than 0.5 mol %, more typically greater than 1 mol %, most typically greater than 2 mol %) components and sulfur contaminants (typically greater than 0.01 mol %, more typically greater than 0.1 mol %, and most typically greater than 1 mol %). The term "C6+" as used herein refers to hydrocarbons having 6 or more carbon atoms, wherein such hydrocarbons may be linear, branched, or cyclic, and may further include at least one double bond. For example, contemplated C6+ hydrocarbons include n-hexane, i-heptane, benzene, toluene, xylene, etc.

In one especially preferred aspect of the inventive subject matter, the absorber in contemplated plants is refluxed at a temperature near or even below the gas hydrate point, and receives a light hydrocarbon liquid from downstream separators as a scrubbing stream, and hot compressed high pressure vapors that are recycled from the condensate stabilizer and flash drums as stripping stream. Therefore, due to the heretofore unprecedented low temperature of the absorber, use of lean oil as scrubbing medium, and hot lean stripping vapor, separation efficiency is drastically improved. Still further, and in contrast to known configurations, the absorber will operate at a pressure of least 600 psig, and even more typically at least 800 psig.

In such configurations, the absorber forms a bottom stream that is further fractionated in a lower pressure stabilizer column for the production of the C6+ condensate. Such configurations allow recovery of at least 95%, more typically 97%, and most typically over 99% of the C6+ and heavy sulfur contaminants from the feed gas. In terms of contaminant levels, it should be noted that aromatic hydrocarbons (e.g., benzene, toluene, and xylenes) are almost completely removed from the feed gas, typically from about 10,000 ppmv down to less than 100 ppmv, and most typically less than 10 ppmv, which thus eliminates foaming and corrosion problems in downstream acid gas removal units.

Viewed form a different perspective, the light portions of the feed gas are separated in the absorber by refluxing the absorber near the hydrate point (e.g., +/−20° F., more typically +/−10° F., most typically +/−7° F.), and by stripping and scrubbing the feed with the vapor components from the stabilizer and separators, while the heavier C6+ liquid components are provided (after flashing) to the stabilizer via the absorber bottom stream. Thus, separators in contemplated plants and methods are preferably fluidly coupled to the refluxed absorber and the condensate stabilizer such that the separators receive liquid products from the refluxed absorber, wherein at least some of the separators are configured to produce flash vapors. In preferred plants, it is contemplated that vapors from the separators are combined with the compressed vapor from the stabilizer to thereby form at least a portion of the stripping vapor that is fed to the refluxed absorber.

In contrast, Prior Art FIG. 1 schematically depicts a known configuration for gas condensate recovery. Here, the hydrocarbon feed is at a pressure of about 1000 psig to about 1200 psig and at a temperature of about 100° F. to about 140° F., and has a composition as indicated in Table 1 below:

TABLE 1

| Component | Mole Fraction |
|---|---|
| H2O | 0.027819 |
| Nitrogen | 0.000487 |
| CO2 | 0.068116 |
| H2S | 0.252029 |
| Methane | 0.451025 |
| Ethane | 0.065099 |
| Propane | 0.033182 |
| i-Butane | 0.009147 |
| n-Butane | 0.017710 |
| i-Pentane | 0.007493 |
| n-Pentane | 0.008952 |
| n-Hexane | 0.011580 |
| n-Heptane | 0.040850 |
| COS | 0.000097 |
| M-Mercaptan | 0.000049 |
| E-Mercaptan | 0.000039 |
| m-Xylene | 0.000973 |
| Benzene | 0.000778 |
| E-Benzene | 0.000195 |
| Toluene | 0.004379 |

In such prior art configuration, the high pressure feed gas stream 1 is mixed with compressor discharge condensate stream 22 and separated in separator 51 (which also produces sour water stream 40). The separator liquid 3 is heat exchanged in exchanger 52 and heater 53 (using heating fluid 94) to streams 4 and 5, respectively, to a temperature of about 150° F. to about 180° F. Stream 5 is then letdown in pressure to about 350 psig to about 450 psig via JT valve 54 forming stream 6, which is separated in separator 55 forming vapor stream 8 and flashed liquid stream 7. Vapor stream 8 is routed to separator 62, where it is mixed with cooled compressor discharge vapor 13 at about 130° F. The gaseous mixture 14 of separator 62 is further compressed in compressor 63 to form compressed stream 15 at about 250° F. The liquid stream 17 from separator 62 is routed to pump 56 and pumped to suitable pressure to form stream 18, which is then fed to separator 65.

The liquid stream 7 from separator 55 is heated in exchanger 56 to about 180° F. to 230° F. forming stream 9 and then fed to condensate stabilizer 57 (via JT valve 67) operating at about 180 psig to 220 psig. The H2S, C2, C3, and lighter components are stripped with side reboiler 58 and bottom reboiler 59, typically using steam 91. The condensate stabilizer produces an overhead gas 11 and a bottom product 10 which is further heat exchanged with incoming feed in exchanger 56 and 52, forming the gas condensate product stream 26 (via streams 24 and 25). The overhead vapor stream 11 is compressed by compressor 60 to form stream 12, cooled in cooler 61 (using cooling medium 92), mixed with flashed vapor stream 8 and separated in separator 62. The separator vapor 14 is further compressed in compressor 63 to stream 15, cooled in cooler 64 via cooling medium 93 to form stream 16, which is then separated in separator 65. The separator liquid stream 19 is pumped with pump 66 forming stream 22 at about 1000 psig to 1200 psig that is further mixed with stream 1 in separator 51. The separator vapor stream 20 is mixed with flashed vapor stream 2 from separator 51 forming the lean gas stream 21 that is further processed in the downstream acid gas removal unit. It should be noted that while such known configurations can recover condensates that meet the vapor pressure specification (Reid Vapor Pressure of 4 psia), the condensate production and recovery levels are typically less than 90% and often fail to produce a product gas depleted of the C6+ and sulfur contaminants.

Figure 2:
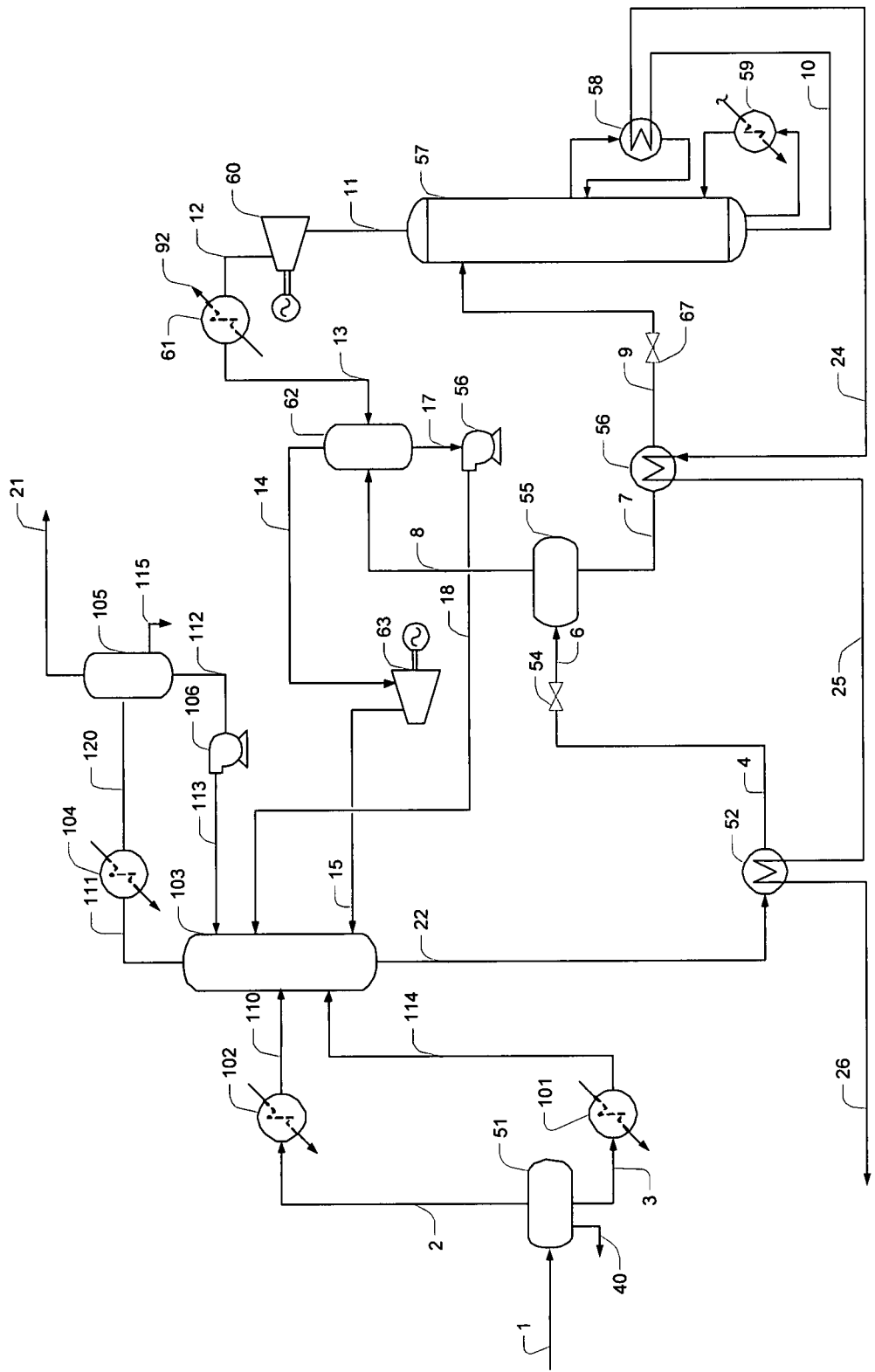
FIG. 2 is a schematic configuration of an exemplary NGL plant according to the inventive subject matter

Conversely, an exemplary configuration according to the inventive subject matter is depicted in FIG. 2. Here, feed stream 1, again at a pressure of about 1000 psig to 1200 psig and a temperature of about 100° F. to about 140° F. is separated in separator 51 into liquid stream 3, vapor stream 2, and sour water stream 40. The sour water stream 40 is typically removed from the separator and routed to the sour water stripper unit (not shown). Vapor stream 2 is heated to about 160° F. to 180° F. in heater 102 and fed as stream 110 to the mid section of refluxed absorber 103, while liquid stream 3 is heated in heater 101 to a temperature of about 170° F. to about 200° F. and fed as stream 114 to the lower section of the absorber 103.

The refluxed absorber 103 preferably includes trays or packing for contacting devices (e.g., a typically absorber will require 12 to 15 contact stages or more), but various alternative configurations are also deemed suitable. To further improve absorption efficiency, condensate 18 that is produced in the inter-stage drum 62 (via stream 17) is used as lean oil for scrubbing while compressed vapor stream 15 from compressor 63 is used as stripping vapor. The absorber 103 produces an overhead vapor stream 111 that is cooled in cooler 104 to about 70° F. to 90° F., or just above the gas hydrate temperature, forming two phase mixture 120 (the hydrate temperature will typically vary with feed gas composition and operating pressure). Regardless of the particular compositions and pressures, it is generally preferred that a low overhead temperature is maintained for separation (which may require external refrigeration; not shown).

The two phase mixture stream 120 is separated in separator 105 into vapor stream 21, hydrocarbon stream 112, and sour water stream 115. The sour water stream 115 is routed to the sour water stripper unit (not shown), and the hydrocarbon stream 112 is pumped by pump 106 forming reflux stream 113. The absorber produces a C6+ depleted vapor product stream 21 and an intermediate stream 22 containing the C6+ and sulfur contaminants. Intermediate stream 22 is further heated in exchanger 52 to about 180° F. to 230° F. forming stream 4, and letdown in pressure to about 350 psig to 450 psig via valve 54 to separator 55 (via stream 6), generating vapor stream 8 and liquid stream 7. The liquid stream 7 is further heated in heater 56 and fed to condensate stabilizer 57 operating at about 180 psig to 220 psig (via stream 9 and JT valve 67).

In the condensate stabilizer, H2S, C2, C3, and lighter components are stripped with side reboiler 58 (using bottom stream 10 as heat source) and bottom reboiler 59. The stabilizer produces an overhead gas 11 and a bottom stream 10 which is further heat exchanged with incoming feed in exchanger 56 and 52, forming the gas condensate product stream 26 (via streams 24 and 25). The overhead vapor stream 11 is compressed by compressor 60 to form stream 12, which is then cooled in cooler 61 using cooling medium 92 to form stream 13. Stream 13 is then mixed with flashed vapor stream 8 and separated in separator 62. The separator 62 produces a vapor 14 is further compressed in compressor 63 forming stripping vapor 15 at about 250° F. to absorber 103. The separator liquid stream 17 is pumped by pump 56 forming stream 18, which is used as lean oil for scrubbing in the refluxed absorber.

It should be particularly recognized that the heat content of the compressor discharge 15 raises the absorber bottom temperature to a temperature that advantageously allows stripping of the C5 and lighter components from the feed streams. This stripping method has eliminated the cooler, separator and pumping on the compressor discharge (i.e., separator 65, pump 66 and exchanger 64 of Prior Art FIG. 1).

Figure 3:
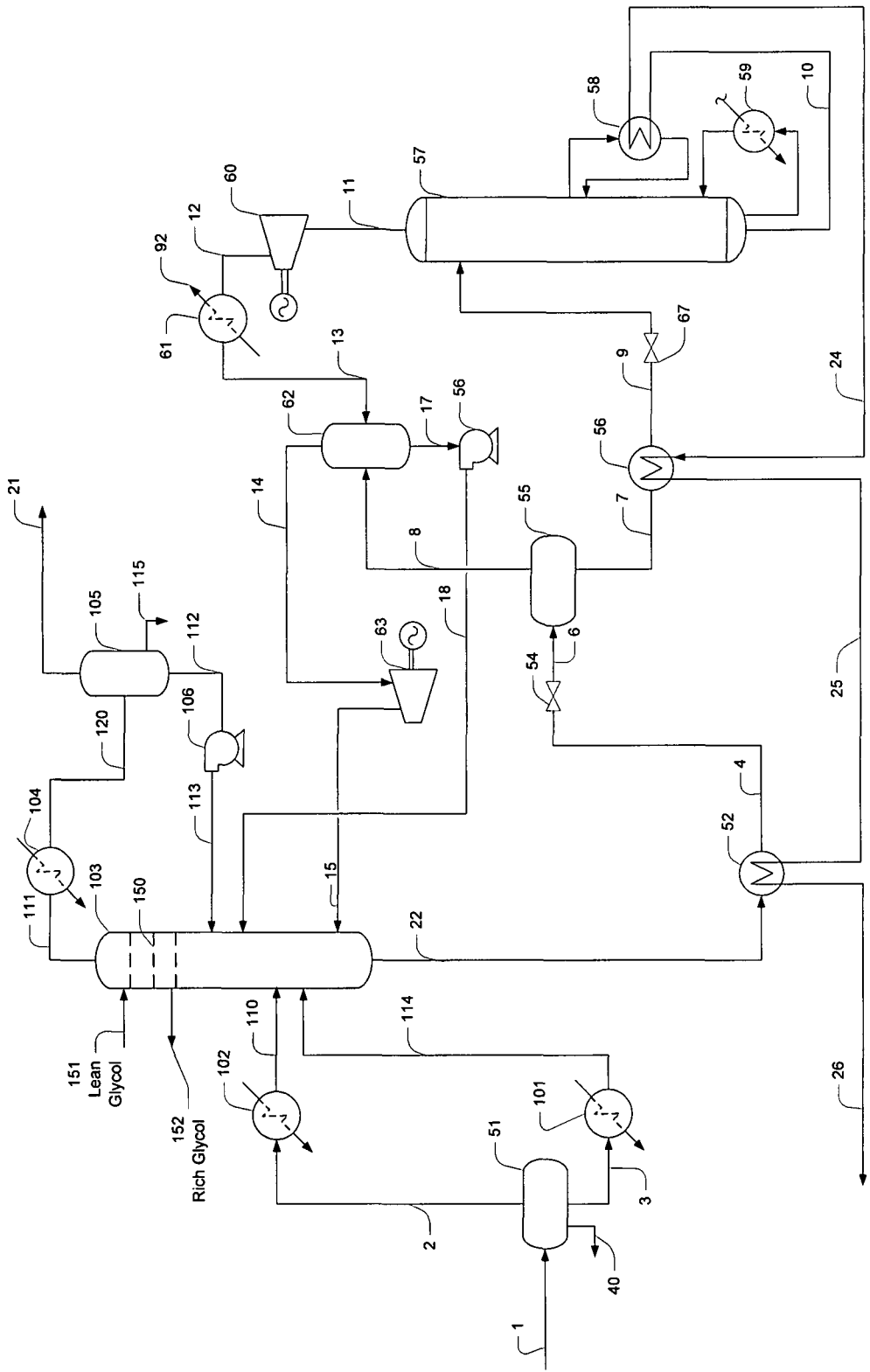
FIG. 3 is a schematic configuration of another exemplary NGL plant according to the inventive subject matter.

Another exemplary configuration according to the inventive subject matter is depicted in FIG. 3 in which the feed gas is chilled to a temperature below its gas hydrate temperature for deeper extraction of the C6+ components. Here, the absorber column 103 comprises a top scrubbing section 150 that is fed with lean glycol stream 151 (typically about 90 wt % or higher) for reduction of the water content of the feed gas from the lower section of the absorber. Water is absorbed by the glycol stream 151 forming rich glycol stream 152 that is withdrawn from the scrubbing section 150. The rich glycol solution is subsequently regenerated by a glycol regeneration unit (not shown) and recycled back to the scrubbing section 150 as lean glycol stream 151. The scrubbing section preferably includes trays or packing for contacting devices (such a bubble cap trays, valve trays, random or structured packing), but various alternative configurations are also deemed suitable. The overhead gas stream 111 from the glycol section is cooled to below the hydrate temperature, typically 40° F. or lower. At such low temperature, over 99.99% of the C6+ components and sulfur contaminants are removed. With respect to remaining elements and operating conditions, the same considerations and numerals as provided in FIG. 2 apply.

A performance calculation of a plant according to FIG. 2 and FIG. 3 of exemplary condensate separation processes is summarized in Table 2 below. The total BTEX (benzene, toulene and xylenes) content of the feed gas 2 and liquid 3 is significantly reduced, from about 6,000 ppmv to about 4 ppmv in the product gas stream 21, which represents a recovery of over 99% of the C6+ hydrocarbons and sulfur contaminants. The significant reduction in the BTEX components in the product gas has virtually eliminated the foaming problems in downstream treating units, while complying with the most stringent sulfur emission regulations.

TABLE 2

| Mole Fraction | Stream Number | | | | |
|---|---|---|---|---|---|
| | 2 | 3 | 21 | 22 | 26 |
| H2O | 0.003800 | 0.003166 | 0.001360 | 0.002894 | 0.000000 |
| Nitrogen | 0.000603 | 0.000096 | 0.000536 | 0.000046 | 0.000000 |
| CO2 | 0.076198 | 0.045125 | 0.075068 | 0.037249 | 0.000000 |
| H2S | 0.248467 | 0.295190 | 0.277624 | 0.287783 | 0.000011 |
| Methane | 0.538301 | 0.169605 | 0.497169 | 0.115035 | 0.000000 |
| Ethane | 0.069033 | 0.057885 | 0.071796 | 0.053801 | 0.000000 |
| Propane | 0.029636 | 0.050910 | 0.036595 | 0.054139 | 0.000084 |
| i-Butane | 0.006714 | 0.019647 | 0.009985 | 0.022826 | 0.001492 |
| n-Butane | 0.011870 | 0.042392 | 0.018881 | 0.051407 | 0.009338 |
| i-Pentane | 0.003805 | 0.022629 | 0.005508 | 0.033359 | 0.038665 |
| n-Pentane | 0.004111 | 0.028713 | 0.005062 | 0.045789 | 0.066720 |
| n-Hexane | 0.003329 | 0.044807 | 0.000200 | 0.060566 | 0.171689 |
| n-Heptane | 0.003140 | 0.191248 | 0.000017 | 0.202883 | 0.616428 |
| COS | 0.000085 | 0.000157 | 0.000107 | 0.000166 | 0.000000 |
| M-Mercaptan | 0.000031 | 0.000121 | 0.000053 | 0.000137 | 0.000012 |
| E-Mercaptan | 0.000018 | 0.000125 | 0.000032 | 0.000164 | 0.000155 |
| m-Xylene | 0.000068 | 0.004582 | 0.000000 | 0.004823 | 0.014691 |
| Benzene | 0.000189 | 0.003148 | 0.000004 | 0.004065 | 0.011674 |
| E-Benzene | 0.000015 | 0.000910 | 0.000000 | 0.000965 | 0.002938 |
| Toluene | 0.000585 | 0.019543 | 0.000000 | 0.021903 | 0.066100 |
| Kgmol/hr | 19,879.2 | 5,155.5 | 23,291.4 | 5,212.5 | 1,700.0 |

It should be especially appreciated that contemplated configurations, when compared to heretofore known configurations and processes, provide the most efficient method for separation and recovery of the C6+ components from feeds, particularly for high pressure gas at 800 psig or higher pressure. Currently known separation methods typically require reducing the feed pressure to 600 psig or lower (to increase the relative volatility between C5 and C6 components for separation purposes) which are energy inefficient and require gas recompression for downstream units operation.

In contrast, it should be appreciated that contemplated configurations will use a refluxed absorber that is fed by lean oil, and that uses an overhead gas recycled from the condensate stabilizer. Additionally, significant reduction in heating and cooling duties can be realized by utilizing waste heat content from the compressor discharge that is normally rejected to the environment, thus reducing heat source (e.g., steam) and eliminating the need for air coolers. Still further, it should be noted that by operationally coupling the refluxed absorber to the condensate stabilizer, the overall gas condensate recovery is significantly improved (over 99% of C6+ recovery) and a clean product gas almost depleted of the C6+ hydrocarbons and sulfur contaminants is produced. It should also be recognized that contemplated configurations may be employed to produce a feed gas that can be efficiently processed in downstream acid gas removal units, NGL recovery units and sulfur plants in refinery and natural gas liquids separation plants. Still further, it should be pointed out that the separation processes produce condensate products that are depleted of the undesirable lighter compounds, e.g., H2S, carbon dioxide, methane, and/or nitrogen. While contemplated configurations can improve condensate recovery in grass root gas plant installation, they can also be used for debottlenecking existing units (e.g., by improving the C6+ condensate recovery and/or eliminating foaming problems in downstream units). Further aspects, configurations, and contemplations for gas condensate separation are disclosed in our copending International patent application (serial number PCT/US05/22298), which was filed Jun. 22, 2005, and which is incorporated by reference herein.

Thus, specific embodiments and applications of NGL recovery have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:

1. A method of processing a high pressure hydrocarbon feed in a refluxed absorber and a stabilizer, wherein the hydrocarbon feed includes at least 0.5 mol % of C6+ hydrocarbons, comprising:
    separating the hydrocarbon feed into a vapor portion and a liquid portion;
    feeding the vapor portion and the liquid portion of the high pressure hydrocarbon feed to the refluxed absorber, cooling an overhead product of the refluxed absorber to produce a two-phase mixture, and separating the two-phase mixture to generate a reflux to the refluxed absorber,
    wherein cooling the overhead product is performed to maintain an overhead temperature of the refluxed absorber at or below hydrate temperature of the hydrocarbon feed;
    wherein the refluxed absorber produces a C6+ enriched bottom product and a C6+ depleted overhead product;

separating the C6+ enriched bottom product in a first separator into a liquid portion of the C6+ enriched bottom product and a vapor portion of the C6+ enriched bottom product;
feeding the liquid portion of the C6+ enriched bottom product to the stabilizer;
feeding the vapor portion of the C6+ enriched bottom product to a second separator;
feeding a stabilizer overhead to the second separator;
feeding a stripping medium to a bottom portion of the refluxed absorber, wherein the stripping medium is at least in part formed from a vapor portion of the stabilizer overhead; and,
feeding a scrubbing medium above the bottom portion of the refluxed absorber, wherein the scrubbing medium is at least in part formed from a liquid portion of the stabilizer overhead.

2. The method of claim 1 wherein the stripping medium further comprises a vapor portion of a bottom product of the refluxed absorber.

3. The method of claim 1 wherein the scrubbing medium further comprises a vapor portion of a bottom product of the refluxed absorber.

4. The method of claim 1 wherein the stripping medium is compressed by a compressor prior to entry into the refluxed absorber.

5. The method of claim 1 wherein the refluxed absorber produces a C6+ enriched bottom product and a C6+ depleted overhead product, further comprising a step of separating the C6+ enriched bottom product in a first separator into a liquid portion of the C6+ enriched bottom product and a vapor portion of the C6+ enriched bottom product, and further comprising a step of feeding the liquid portion of the C6+ enriched bottom product to the stabilizer.

6. The method of claim 5 further comprising a step of feeding the vapor portion of the C6+ enriched bottom product to a second separator.

7. The method of claim 6 further comprising a step of feeding the stabilizer overhead to the second separator.

8. The method of claim 1 further comprising a step of providing a dehydrating section to the refluxed absorber and maintaining the overhead temperature of the refluxed absorber below hydrate temperature of the hydrocarbon feed.

9. The method of claim 1 wherein the high pressure hydrocarbon feed has a pressure of between 800 and 1200 psig.

10. A gas treatment plant comprising:
a feed gas separator configured to receive a C6+ containing feed gas and further configured to produce a liquid portion and vapor portion;
a refluxed absorber that is configured to receive the liquid portion and vapor portion of the C6+ containing feed gas at a pressure of equal or greater than 600 psig, and that is further configured to produce a C6+ enriched bottom product and a C6+ depleted overhead product;
a condenser fluidly coupled to the refluxed absorber and configured to receive and cool the C6+ depleted overhead product to thereby form a two-phase mixture, and a reflux separator configured to separate a liquid reflux from the C6+ depleted overhead product;
a first separator fluidly coupled to the refluxed absorber to receive the C6+ enriched bottom product and to produce a liquid portion of the C6+ enriched bottom product and a vapor portion of the C6+ enriched bottom product;
a stabilizer fluidly coupled to the first separator and configured to receive the liquid portion of the C6+ enriched bottom product and to produce an overhead;
a second separator fluidly coupled to the stabilizer to receive the overhead and to produce a vapor portion of the overhead and a liquid portion of the overhead;
wherein the refluxed absorber is further configured to receive the vapor portion of the overhead as stripping medium at a bottom portion of the refluxed absorber, and to receive the liquid portion of the overhead as a scrubbing medium above the bottom portion of the refluxed absorber; and
wherein the condenser is configured to cool the C6+ depleted overhead product to a temperature effective to maintain an overhead temperature of the refluxed absorber at about or below hydrate temperature of the hydrocarbon feed.

11. The plant of claim 10 further comprising a first compressor fluidly coupled to the second separator and configured to compress the vapor portion of the overhead prior to entry into the refluxed absorber.

12. The plant of claim 10 further comprising a conduit fluidly coupled to the first and second separators to feed the vapor portion of the C6+ enriched bottom product from the first separator to the second separator.

13. The plant of claim 10 further comprising a pressure reduction device that is fluidly coupled to the refluxed absorber and first separator and configured to provide a flashed C6+ enriched bottom product to the first separator.

14. The plant of claim 10 further comprising a second compressor fluidly coupled to the stabilizer and configured to compress the vapor portion of the overhead prior to entry into the second separator.

15. The plant of claim 10 wherein the refluxed absorber further comprises a glycol dehydration unit.

16. The plant of claim 10 wherein the refluxed absorber is configured to operate at a pressure of about 1000 psig to 1200 psig.

17. The plant of claim 10 wherein the refluxed absorber is configured to separately receive the vapor portion of a feed gas and the liquid portion of the feed gas.

* * * * *